United States Patent [19]

Inoue et al.

[11] 4,283,554

[45] Aug. 11, 1981

[54] PROCESS FOR PRODUCTION OF β-CHLOROALANINE

[75] Inventors: Chozo Inoue; Soyao Moriguchi, both of Yokohama, Japan

[73] Assignee: Showa Denko Kabushiki Kaisha, Tokyo, Japan

[21] Appl. No.: 154,379

[22] Filed: May 29, 1980

[30] Foreign Application Priority Data

Jun. 8, 1979 [JP] Japan .................................. 54/71165

[51] Int. Cl.$^3$ ............................................ C07C 101/10
[52] U.S. Cl. ............................... 562/574; 260/465.5 R
[58] Field of Search ............................. 562/574, 575

[56] References Cited

FOREIGN PATENT DOCUMENTS 233541  4/1959  Australia ................................ 562/574
46-3964 1/1971  Japan .................................... 562/574

*Primary Examiner*—Joseph E. Evans
*Assistant Examiner*—Michael Shippen
*Attorney, Agent, or Firm*—McAulay, Fields, Fisher, Goldstein & Nissen

[57] ABSTRACT

A novel production process of β-chloroalanine from chloroacetaldehyde is provided. In this process, a bisulfite or sulfite addition compound of chloroacetaldehyde is first reacted, in an aqueous solution, with ammonia and, then, reacted with hydrocyanic acid or a salt thereof. Thus, α-amino-β-chloropropionitrile is formed. This α-amino-β-chloropropionitrile is hydrolyzed under an acidic condition to form β-chloroalanine.

4 Claims, 5 Drawing Figures

PROCESS FOR PRODUCTION OF β-CHLOROALANINE

The present invention relates to a process for preparing β-chloroalanine. More specifically, it relates to a process for preparing β-chloroalanine by reacting a bisulfite or sulfite addition compound of chloroacetaldehyde, in an aqueous solution, first with ammonia and, then, with hydrocyanic acid or a salt thereof, followed by hydrolysis of the formed α-amino-β-chloropropionitrile under an acidic condition.

Beta-chloroalanine itself is one of amino acids having physiological activity (cf. J. Biol. Chem. 252, 3170). Beta-chloroalanine is also useful as an intermediate for the syntheseis of, for example, various pharmaceutical compounds and pesticidal compounds, such as, antibiotics (e.g. cycloserine) and sulfur-containing amino acids (e.g. cystine) or cystein.

However, since a production process of β-chloroalanine, which would be industrially advantageous from an economical point of view, has not been known, β-chloroalanine is not widely used so an intermediate for the synthesis of pharmaceutical compounds and pesticides. For instance, known methods for producing β-chloroalanine are a method for substituting chlorine for the hydroxyl group of serine (cf. J. Chem. Soc. p. 1968, 1969) and a method for the chlorination of cystine (cf. Ber. 93, p 782, 1960). However, since expensive starting materials are used in these methods, these methods are not suitable for use in the industrial production of β-chloroalanine.

Furthermore, a so-called Strecker synthesis is well-known for the industrial synthesis of amino acids. However, β-chloroalanine has not been obtained from the corresponding aldehyde, chloroacetaldehyde, by Strecker synthesis. That is, when chloroacetaldehyde is reacted with hydrocyanic acid and ammonia, β-chlorolactonitrile, which is formed by the addition of a cyano group of chloroacetaldehyde, is produced. However, since the amination of the hydroxyl group of the formed, β-chlorolactonitrile with ammonia is extremely difficult, the desired α-amino-β-chloropropionitrile which is the intermediate for the synthesis of β-chloroalanine cannot be obtained. Even in the case where chloroacetaldehyde is first reacted with ammonia to form α-amino-β-chloroethanol and then reacted with hydrocyanic acid or the salts thereof, α-amino-β-chloropropionitrile cannot be formed, but β-chlorolactonitrile is formed by the replacement of the amino group of α-amino-β-chloroethanol with a cyano group. Furthermore, in the case where β-chlorolactonitrile is reacted with concentrated ammonia under severe reaction conditions for the purpose of the production of α-amino-β-chloropropionitrile, the decomposition of β-chlorolactonitrile occurs.

Accordingly, an object of the present invention is to obviate the above-mentioned problems of the prior arts and to provide a process for preparing β-chloroalanine from chloroacetaladehyde at a high selectivity.

Other objects and advantages of the present invention will be apparent from the description set forth hereinbelow.

In accordance with the present invention, there is provided a process for preparing β-chloroalanine comprising the steps of:

(a) reacting an aqueous solution of a bisulfite or sulfite addition compound of chloroacetaldehyde with ammonia and, then, with hydrocyanic acid or a salt thereof, whereby α-amino-β-chloropropionitrile is formed, and (b) hydrolyzing the resultant α-amino-β-chloropropionitrile under an acidic condition.

The present invention will be better understood from the description set forth below with reference to the accompanying drawings wherein.

The bisulfite addition compound of chloroacetaldehyde can be readily obtained by reacting approximately equimolar amounts of chloroacetaldehyde and bisulfite with each other in an aqueous solution at room temperature. Any water-soluble bisulfites can be used in the formation of the bisulfite addition compound of chloroacetaldehyde. Examples of the typical bisulfites are: alkali metal salts such as lithium, sodium, potassium and the like; alkaline earth metal salts such as calcium, magnesium and the like; and an ammonium salt. The most preferable bisulfite is ammonium bisulfite.

Although the amounts of the bisulfites and the chloroacetaldehyde used in the formation of the bisulfite addition compounds may be varied over a wide range, the molar ratio of bisulfite to chloroacetaldehyde is preferably 1:0.8–1.2. Although a further excess amount of either compound can be used, the use of an excess amount of either component not only causes no advantageous result, but is also uneconomical. Further, there is a fear that the use of an excess amount of either component produces undesirable by-products.

In lieu of the bisulfites, ammonium sulfite can be used in the formation of the sulfite addition compound of chloroacetaldehyde. However, the use of the other sulfites, such as alkali metal sulfites and alkaline earth metal sulfites, is not suitable in the formation of the sulfite addition compound of chloroacetaldehyde, since the formed sulfite addition compound does not form the desired α-amino-β-chloroethane sulfonates at a good yield, in the subsequent reaction step. Similarly, in the case where bisulfite is reacted with chloroacetaldehyde under an alkaline condition, ammonium bisulfite should be used. This is because, when bisulfite is reacted with chloroacetaldehyde under an alkaline condition, the corresponding sulfite is substantially reacted with chloroacetaldehyde to form the sulfite addition compound of chloroacetaldehyde.

Figure 1:
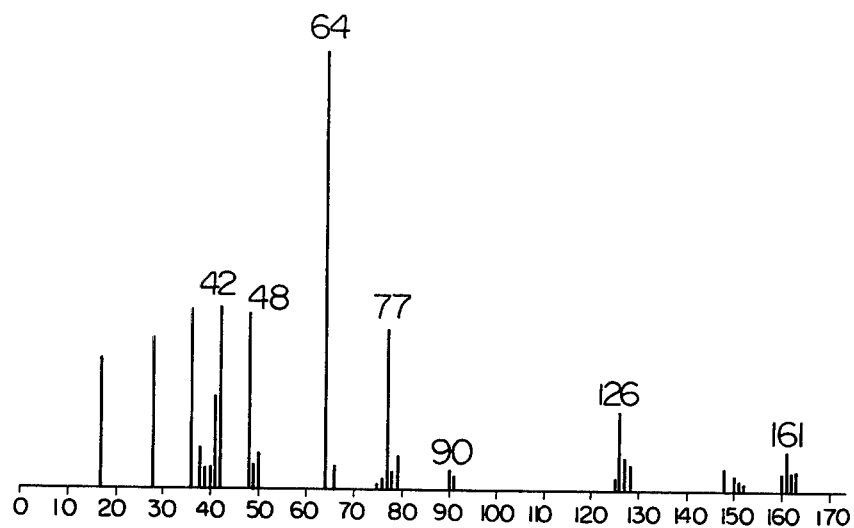
FIGS. 1 and 2 illustrate the mass spectrum and IR spectrum of the intermediate, α-amino-β-chloroethane sulfonic acid, respectively.
Figure 2:
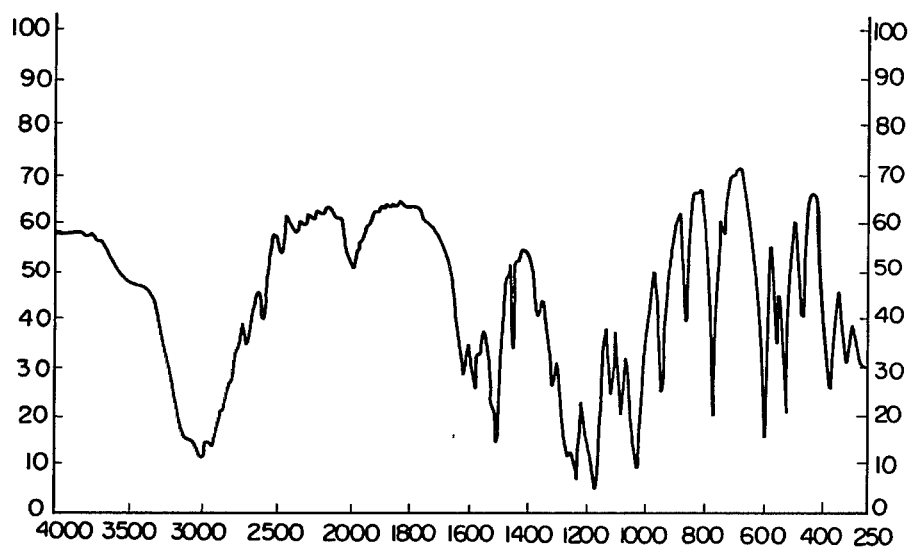

The bisulfite (or sulfite) addition compound of chloroacetaldehyde is, then, reacted with ammonia in an aqueous medium. The ammonia can be used in the form of gaseous ammonia, liquid ammonia or the aqueous solution thereof. Although the amount of ammonia used in the reaction may be varied depending upon the kinds of the bisulfites and the sulfite and gaseous ammonia, liquid ammonia or the aqueous solution thereof, the molar ratio of ammonia to chloroacetaldehyde should be preferably within the range of from 1 to 5, more preferably 2 to 4. Although there is no critical reaction temperature or reaction time, this reaction is generally carried out within a temperature of from 0° to 50° C., more preferably 20° to 30° C. for 0.5 through 2 hours. Thus, α-amino-β-chloroethane sulfonates ClCH$_2$CH(NH$_2$)SO$_3$M (M=NH$_4$, Na, K, ½Ca, ½Mg etc.) are obtained. These α-amino-β-chloroethane sulfonates and α-amino-β-chloroethane sulfonic acid are novel compounds. The α-amino-β-chloroethane sulfonic acid or the salts thereof can be recovered from the aqueous solution containing the same by neutralizing the excess amount of ammonia with a mineral acid (e.g. sulfuric acid, hydrochloric acid) and by lowering the pH of the solution to an isoelectric point. The mass spectrum and IR spectrum of the α-amino-β-chloroethane sulfonic acid ClCH$_2$CH(NH$_2$)SO$_3$H are illustrated in FIGS. 1 and 2, respectively.

The result of elemental analysis of α-amino-β-chloroethane sulfonic acid thus obtained is as follows.

Found: H 3.71%; C 15.31%; N 8.17%; Cl 21.84%; Calculation (as C$_2$H$_6$NO$_3$SCl): H 3.79%; C 15.05%; N 8.78%; Cl 22.22%.

The α-amino-β-chloroethanesulfonate obtained by the reaction of the bisulfite (or sulfite) addition compound of chloroacetaldehyde and ammonia is reacted with hydrocyanic acid or the salts thereof (e.g. alkali metal salts, alkaline earth metal salts or ammonium salt) to form α-amino-β-chloropropionitrile. Since α-amino-β-chloropropionitrile is a very unstable substance, especially in an aqueous solution, special caution must be taken during the process of this reaction.

For example, the reaction is carried out by using a suitable organic solvent, which is not miscible with water, so that the formed α-amino-β-chloropropionitrile is rapidly transferred into an organic phase. Of course, once α-amino-β-chloroethane sulfonate is separated from an aqueous reaction mixture, the separated α-amino-β-chlorethane sulfonate can be reacted with hydrocyanic acid or the salts thereof in a suitable organic solvent. Preferably, while the reaction is carried out by using an apparatus in which a reactor is connected with an extractor and a decanter, the α-amino-β-chloropropionitrile produced in the reaction is continuously extracted with a suitable organic solvent from the aqueous reaction mixture.

The organic solvents used in this reaction should be those which are stable under the reaction conditions, which neither react with nor decompose the reactants or the product, which do not readily dissolve the reactants, but readily dissolve the product, and which do not react with hydrogen chloride. Examples of such an organic solvent are carbon tetrachloride, chloroform, methylene chloride, trichloroethylene, n-hexane, n-pentane, cyclohexane, diethyl ether, diisopropyl ether, benzene, toluene, xylene, chlorobenzene, ethylbenzene and the like. The most preferable organic solvent is ethylacetate, ethyleneglycol monoethyl ether acetate, propionitrile or porpylene carbonate.

The amount of hydrocyanic acid or the salts thereof (e.g. sodium cyanide, potassium cyanide) used in this reaction is preferably a stoichiometric amount or more. Practically speaking, the amount of hydrocyanic acid or the salts thereof is, more preferably, within the range of from 2.0 to 5.0 mol, based on 1 mol of α-amino-β-chloroethane sulfonate. Although there is no critical reaction temperature or reaction time, the reaction is preferably carried out at a temperature of from 0° to 30° C., more preferably 5° to 10° C., for 5 through 24 hours.

The obtained α-amino-β-chloropropionitrile and the salts thereof are also novel compounds. Since the resultant α-amino-β-chloropropionitrile is an unstable substance, the product is recovered, as hydrochloride, by introducing dry hydrogen chloride gas into the organic solution containing the same. The α-amino-β-chloropropionitrile hydrochloride is precipitated, as crystals, in the organic solution and can be isolated in a known manner.

Figure 3:
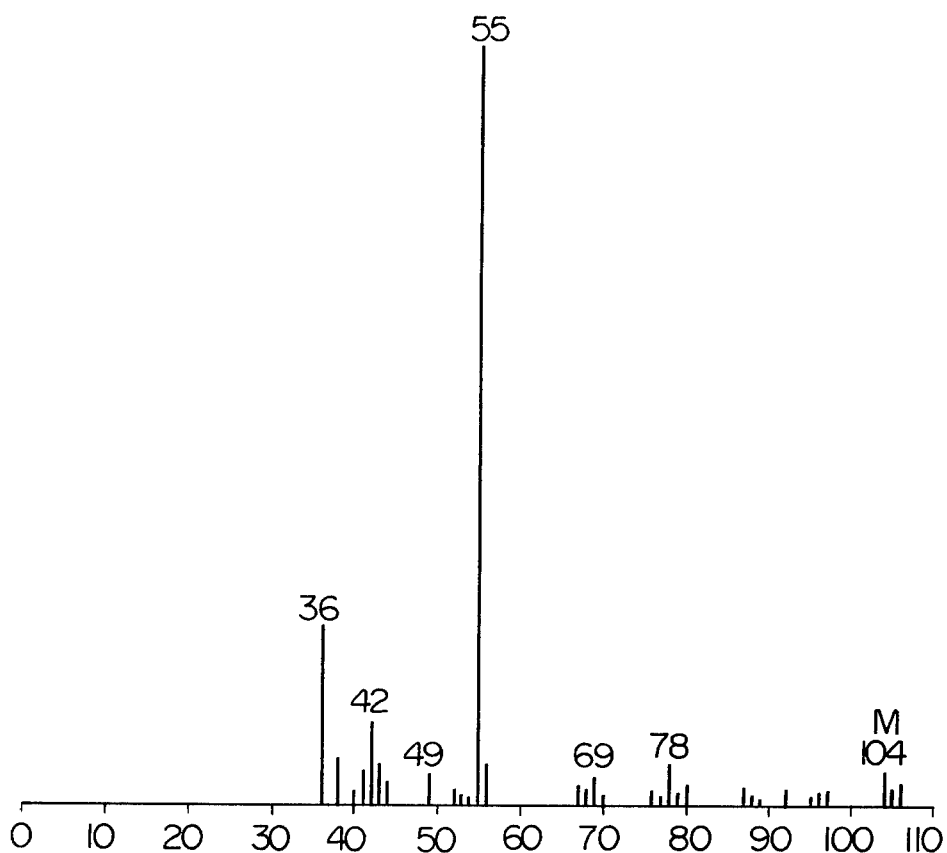
FIG. 3 illustrates the mass spectrum of the intermediate, α-amino-β-chloropropionitrile.
Figure 4:
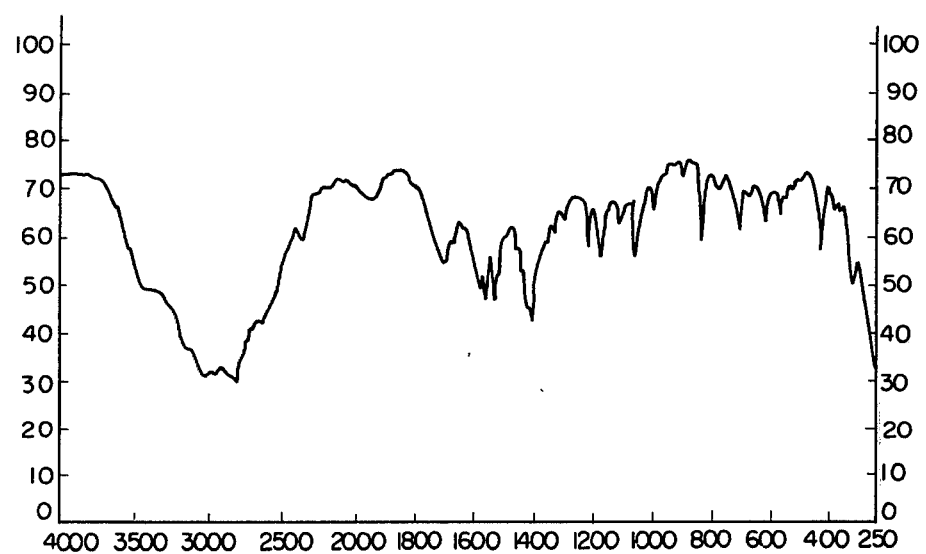
FIG. 4 illustrates the IR spectrum of α-amino-β-chloropropionitrile hydrochloride.
Figure 5:
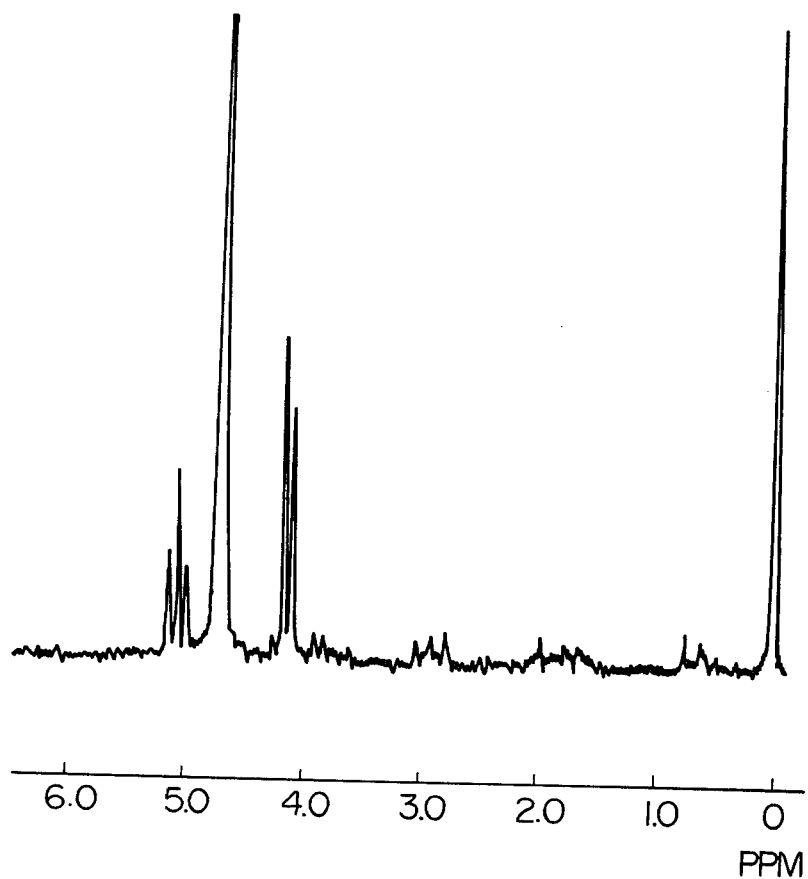
FIG. 5 illustrates the NMR spectrum of α-amino-β-chloropropionitrile.

The mass spectrum of α-amino-β-chloropropionitrile thus obtained is illustrated in FIG. 3. The IR spectrum of α-amino-β-chloropropionitrile hydrochloride is illustrated in FIG. 4 and the NMR spectrum of α-amino-β-chloropropionitrile is illustrated in FIG. 5.

The result of an elemental analysis of α-amino-β-chloropropionitrile hydrochloride is as follows.

Found: H 4.80%; C 24.05%; N 19.60%; Cl 53.00%; Calculation (as C$_3$H$_6$N$_2$Cl$_2$): H 4.29%; C 25.56%; N 19.87%; Cl 50.29%.

According to the present invention, the formed α-amino-β-chloropropionitrile in an organic solution is hydrolyzed by the addition of mineral acids, such as hydrychloric acid, sulfuric acid, nitric acid and the like, after the aqueous solution phase, if present, is separated from the organic solution phase. The organic solution is heated to evaporate the organic solvent off and, then, is subjected to hydrolysis under an acidic condition at a temperature of, for example, 80° through 100° C. for 0.5 through 2 hours. Thus, β-chloroalanine is formed in an aqueous mineral salt solution. The β-chloroalanine can be recovered as follows.

For instance, the aqueous solution containing β-chloroalanine is first concentrated and, then, alcohols, such as methanol, ethanol and the like, are added thereto. Thus, the ammonium salt of the mineral acids are crystallized out of the solution. The resultant alcohol solution is separated from the crystallized ammonium salt and, then, a suitable solvent, such as an ether, is added to the separated alcohol solution to crystallize the mineral acid salt of β-chloroalanine. The crystals can be purified by a conventional technique, such as recrystallization. Furthermore, if necessary, β-chloroalanine can be recovered, as a free amino acid, by the neutralization of the alcohol solution of the mineral acid salt of β-chloroalanine with an equimolar amount of, for example, pyridine and triethylamine.

According to the present invention, β-chloroalanine can be obtained at a very high selectivity without causing any substantial formation of β-chlorolactic acid.

In addition, when carbon dioxide is added to the α-amino-β-chloropropionitrile solution prior to the hydrolysis of the α-amino-β-chloropropionitrile under an acidic condition, the α-amino-β-chloropropionitrile can be stabilized and, therefore, β-chloroalanine having a high purity can be obtained at a high yield by the hydrolysis of α-amino-β-chloropropionitrile. The carbon dioxide can be used either in the form of a gas or a solid. Although there is no critical amount of carbon dioxide introduced into the aqueous α-amino-β-chloropropionitrile solution, generally speaking, the amount of the carbon dioxide is such that the pH of the aqueous solution becomes 7 through 6 or such that the absorbed amount of the carbon dioxide becomes 0.5 through 1.0 mol based on 1 mol of the α-amino-β-chloropropionitrile. In order to accelerate the absorption of the carbon dioxide, the aqueous α-amino-β-chloropropionitrile solution can be cooled to a temperature of 10° C. or less. Since the absorption rate of the carbon dioxide increases with the increase in the concentration of the aminonitrile, the concentration of the aminonitrile is advantageously adjusted to 20 through 60%, more preferably 40 through 50%.

The present invention is now illustrated by, but is by no means limited to, the following examples, in which all percentages are expressed on a weight basis unless otherwise noted.

EXAMPLE 1

32 g of sodium bisulfite addition compound of chloroacetaldehyde was dissolved in a mixture of 50 ml of 28% concentrated ammonia water and 50 ml of water and the resultant mixture was allowed to react for 1 hour at room temperature. To the reaction mixture 100 ml of ethyl ether was added. After that, 10 g of sodium cyanide dissolved in 30 ml of water was dropwise added to the reaction mixture over 15 minutes, while the reaction mixture was maintained at a temperature of $-10°$ C. Then, while the reaction mixture was maintained at a temperature of from $-5°$ C. to $5°$ C., the reaction mixture was allowed to react for 6 hours with vigorous agitation.

After the completion of the reaction, the reaction mixture was allowed to stand, whereby the ether solution was separated. After removing the ether solution from the aqueous solution, the resultant aqueous solution was extracted with 100 ml of fresh ether. The ether solutions were combined and, then, 50 ml of concentrated hydrochloric acid was gradually added thereto. After that, ether was distilled off and the resultant aqueous solution was heated and concentrated on a boiling water bath for 1 hour. To the concentrated aqueous solution, 30 ml of ethanol was added, whereby ammonium chloride was precipitated. To the separated ethanol solution, 100 ml of ether was added to precipitate 14 g of β-chloroalanine hydrochloride. The mol yield of the β-chloroalanine thus obtained was 50%.

EXAMPLE 2

47 g of 50% aqueous solution of chloroacetaldehyde was mixed with 60 g of 50% aqueous solution of ammonium bisulfite and, then, the mixture was allowed to react for 1 hour at room temperature. 50 ml of 28% ammonia water was added to the mixture and was allowed to react for a further 1 hour at room temperature. After that, 100 ml of ethyl ether was added and, then, 50 ml of an aqueous solution containing 14.7 g of sodium cyanide was dropwise added thereto over 15 minutes under vigorous agitation, while the reaction mixture was kept at a temperture of 10° C. or less. The reaction mixture was allowed to react for 12 hours. After the completion of the reaction, the reaction mixture was treated in a manner as described in Example 1. Thus, 25.5 g of β-chloroalanine hydrochloride was obtained.

EXAMPLE 3

32 g of sodium bisulfite was dissolved in 60 ml of water and, then, 26.3 g of the hemi-hydrate crystal of chloroacetaldehyde was added thereto. After that, the mixture was allowed to react for 2 hours at room temperature. 60 ml of 28% ammonium water was added to the reaction mixture and, then, the reaction mixture was allowed to react for a further 1 hour at room temperature.

The reaction mixture thus obtained was treated in a manner as described in Example 1, except that triethyl amine was added to the alcholic solution of β-chloroalanine hydrochloride, in lieu of ethyl ether, at the final step. Thus, the crystals of β-chloroalanine were precipitated by neutralization. The yield of β-chloroalanine was 22 g.

EXAMPLE 4

54 g ammonium bisulfite addition compound of chloroacetaldehyde was dissolved in 50 ml of water and, then, 60 ml of ammonia water was added thereto. This mixture was allowed to react for 1 hour at room temperature. After 100 ml of ethyl ether was added to the reaction mixture, 50 ml of an aqueous sodium cyanide solution containing 14.7 g of sodium cyanide was dropwise added to the reaction mixture over 15 minutes, while the reaction mixture was maintained at a temperature of 10° C. or less. The reaction mixture was allowed to react for 15 hours at a temperature of 10° C. with vigorous agitation.

After the completion of the reaction, the separated ether solution was removed from the aqueous solution and the resultant aqueous solution was extracted with 100 ml of fresh ether. The ether solutions were combined and, then, the combined solution was dried over anhydrous magnesium sulfate.

After the desiccant was removed, dry hydrogen chloride was introduced into the ether solution, while cooling with ice-water, whereby the ether solution was saturated with hydrogen chloride. Thus, α-amino-β-chloropropionitrile hydrochloride was precipitated. The crystals thus precipitated were separated from ether and dissolved in 30 ml of concentrated hydrochloric acid solution. The solution was heated and concentrated on a boiling water bath for 1 hour. To the concentrate, 50 ml of ethanol was added and the insoluble ammonium chloride was separated. 150 ml of ethyl ether was added to the resultant ethanol solution. Thus, 30 g of β-chloroalanine hydrochloride crystals were obtained.

EXAMPLE 5

26.3 g (0.3 mol) of hemi-hydrate crystals of chloroacetaldehyde were completely dissolved in 62 g (0.31 mol) of a 50% aqueous ammonium bisulfite solution. This aqueous solution was placed in a reactor provided with a perforated plate therein and connected to a decanter. To this aqueous solution, 100 ml of 30% aqueous solution of ammonia was added and, further, ammonia gas was introduced, whereby the aqueous solution was saturated with ammonia. After that, the aqueous solution was allowed to react for 2 hours at room temperature. The reaction mixture was cooled to 10° C. While the reaction mixture was maintained at a temperature of 10° C. and while ammonia gas was introduced into the reaction mixture, 19.7 ml (0.6 mol) of a 50% hydrocyanic acid was added to the reaction mixture. After the addition of the hydrocyanic acid, methylene chloride was introduced into the reaction mixture, while the reaction mixture was vigorously stirred. The methylene chloride layer was collected below the perforated plate fixed to the bottom portion of the reactor. The methylene chloride layer was successively siphoned to the decanter, wherein the aqueous layer was separated from the methylene chloride layer and was returned to the reactor. The separated methylene chloride solution was withdrawn from the decanter and collected in a reservoir.

In a manner as mentioned above, the extraction reaction were carried out for 3 hours, while methylene chloride was introduced into the reaction mixture at a rate of 5 ml/min. Thus, 900 ml of methylene chloride was introduced. During the extraction reaction, the reaction mixture was maintained at a temperature of 10° C.

The methylene chloride solution collected in the reservoir was distilled off at a temperature of 20° through 30° C. under a reduced pressure and the resultant liquid α-amino-β-chloropropionitrile was dissolved in 40 ml of distilled water in another vessel. Carbon dioxide gas was introduced into the mixture for 30 minutes with vigorous stirring. After the introduction of the carbon dioxide, the pH of the mixture became 7. Therefore, 100 ml of concentrated hydrochloric acid solution was added to the mixture and, then, the mixture was hydrolyzed for 1 hour at a temperature of 95° C. After the hydrolysis, the reaction mixture was evaporated to a dry state. The residue was extracted with 100 ml of absolute ethanol and the insoluble ammonium chloride was removed. Ethanol was distilled off. As a result, 31.2 g of chloroalanine hydrochloride were obtained. The yield was 65%.

What we claim is:

1. A process for preparing β-chloroalanine comprising the steps of:
   (a) reacting an aqueous solution of a bisulfite or sulfite addition compound of chloroacetaldehyde with ammonia and, then, with hydrocyanic acid or a salt thereof, whereby α-amino-β-chloropropionitrile is formed, and
   (b) hydrolyzing the resultant α-amino-β-chloropropionitrile under an acidic condition.

2. A process as claimed in claim 1, wherein said bisulfite addition compound of chloroacetaldehyde is derived from the reaction of a water-soluble bisulfite and chloroacetaldehyde.

3. A process as claimed in claim 2, wherein said water-soluble bisulfite is selected from the alkali metal salts, the alkaline earth metal salts and an ammonium salt.

4. A process as claimed in claim 1, wherein said sulfite addition compound of chloroacetaldehyde is derived from the reaction of ammonium sulfite and chloroacetaldehyde.

* * * * *